(12) United States Patent
Ohkawa et al.

(10) Patent No.: US 6,348,485 B1
(45) Date of Patent: Feb. 19, 2002

(54) METHOD FOR TREATING OR PREVENTING SLEEP DISORDERS

(75) Inventors: Shigenori Ohkawa, Takatsuki; Masaomi Miyamoto, Takarazuka, both of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/700,405
(22) PCT Filed: Jun. 8, 1999
(86) PCT No.: PCT/JP99/03057
§ 371 Date: Nov. 14, 2000
§ 102(e) Date: Nov. 14, 2000
(87) PCT Pub. No.: WO99/63977
PCT Pub. Date: Dec. 16, 1999

(30) Foreign Application Priority Data

Jun. 9, 1998 (JP) .......................................... 10-160270

(51) Int. Cl.[7] .................... A61K 31/415; A61K 31/495; A61K 31/55
(52) U.S. Cl. ........................ 514/394; 514/215; 514/221; 514/249
(58) Field of Search ............................. 514/394, 249, 514/215, 221

(56) References Cited

U.S. PATENT DOCUMENTS

| | | |
|---|---|---|
| 3,862,149 A | 1/1975 | Cotrel et al. |
| 3,987,052 A | 10/1976 | Hester |
| 4,094,984 A | 6/1978 | Weber et al. |
| 4,794,185 A | 12/1988 | Rossey et al. |
| 5,786,357 A * | 7/1998 | Young et al. ................. 514/249 |
| 6,034,239 A * | 3/2000 | Ohkawa et al. ............. 544/147 |
| 6,071,928 A * | 6/2000 | Curtis et al. ................. 514/278 |

FOREIGN PATENT DOCUMENTS

| | | |
|---|---|---|
| EP | 0513702 A2 | 11/1992 |
| WO | WO 97/32871 | 9/1997 |

OTHER PUBLICATIONS

A. A. Piergies et al., "The effect of co–administration of zolpidem with fluoxetine: pharmacokinetics and pharmacodynamics", International Journal of Clinical Pharmacology and Therapeutics, vol. 34, No. 4 pp. 178–183(1996).

L. Feerini–Strambi et al., "Effect of Melatonin on Sleep Microstructure: Preliminary Results in Healthy Subjects", Sleep, vol. 16, No. 8, pp. 744–747 (1993).

* cited by examiner

Primary Examiner—Zohreh Fay
Assistant Examiner—Brian-Yong Kwon
(74) Attorney, Agent, or Firm—Mark Chao; Elaine M. Ramesh

(57) ABSTRACT

The present invention provides a pharmaceutical composition for treating or preventing sleep disorders which comprises (S)-N-[2-(1,6,7,8-tetrahydro-2H-indeno[5,4-b]furan-8-yl)ethyl]propionamide in combination with at least one active component selected from zolpidem, zopiclone, triazolam and brotizolam.

2 Claims, 1 Drawing Sheet

METHOD FOR TREATING OR PREVENTING SLEEP DISORDERS

This application is the National Stage of International Application No. PCT/JP99/03057, filed on Jun. 8, 1999.

1. Technical field

The present invention relates to a pharmaceutical composition for treating or preventing sleep disorders which comprises (S)-N-[2-(1,6,7,8-tetrahydro-2H-indeno[5,4-b]furan-8-yl)ethyl]propionamide in combination with at least one active component selected from zolpidem, zopiclone, triazolam and brotizolam.

2. Background art

Sleep disorders can be classified into about 90 different types based on features of the symptoms, cause of the disease, etc. (International Classification of Sleep Disorders (ICSD): In Diagnostic and Coding Manual; American Sleep Disorder Association: Allen Press Inc.: Lawrence, Kans., 1990). Most of the medicines for treating these disorders at present are benzodiazepines and their derivatives. Non-benzodiazepines such as zolpidem, zopiclone, etc., which are comparatively new hypnotics, are structurally different from benzodiazepines, but exhibit the same activities as benzodiazepines through benzodiazepine receptors. It is believed that benzodiazepines lower the activity of information processing by sedating the limbic system and hypothalamus and inducing sleep. Further, it is known that benzodiazepines do not increase REM (rapid eye movement) sleep and increase non-REM sleep only.

On the other hand, it is disclosed in WO 97/32871 that various tricyclic compounds including (S)-N-[2-(1,6,7,8-tetrahydro-2H-indeno[5,4-b]furan-8-yl)ethyl]propionamide, have an excellent activity as melatonin agonists and are useful for treating or preventing sleep disorders, etc.

DISCLOSURE OF THE INVENTION

Figure 1:
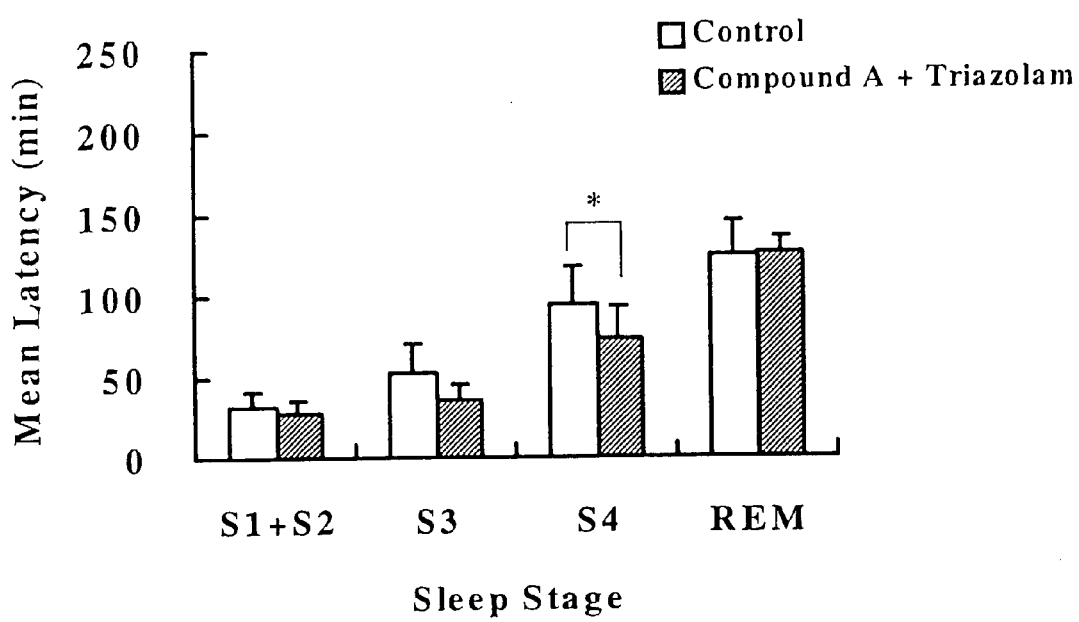
FIG. 1: Effects of compound A and triazolam on sleep latencies at nighttime in monkeys. Each value shows the mean latency to appear of each sleep stage (SEM). S1+S2: stage 1 and stage 2; S3: stage 3; S4: stage 4 and REM: rapid eye movement. *$P<0.05$ compared with control group (paired t-test).

It is indicated that known hypnotics have many problems such as transient insomnia (rebound insomnia) [Science, Vol.201, pages 1039–1041, 1978], dysmnesia such as anterograde amnesia [Psychopharmacology, Vol.70, pages 231–237, 1980, Neuroscience and Biobehavior Review, Vol.9, Pages 87–94, 1985], ataxia after awaking from sleep and somnolence. Therefore, it is desired to develop a hypnotic without these problems.

The inventors of the present invention made intensive studies and as a result, they found that (S)-N-[2-(1,6,7,8-tetrahydro-2H-indeno[5,4-b]furan-8-yl) ethyl]propionamide (hereinafter referred to as compound A) in combination with at least one active component selected from zolpidem, zopiclone, triazolam and brotizolam (as a pharmaceutical mixture, combination dosage form or concomitant pharmacotherapy) produces clinically beneficial effects as a medication exhibiting remarkable efficacy in the therapy (treating) and prophylaxis (preventing) of sleep disorders with substantially no risk for side effects such as recoil insomnia, dysmnesia, ataxia after awaking from sleep and somnolence and hence is safer than monotherapy using any of the above-mentioned active components. The present invention has been developed on the basis of the above finding.

Namely, the present invention provides a pharmaceutical composition for treating or preventing sleep disorders which comprises compound A in combination with at least one active component selected from zolpidem, zopiclone, triazolam and brotizolam, a method for reducing amounts and(or) side effects of benzodiazepines administered to a mammal which comprises administering to such mammal an effective amount of melatonin agonists in combination with benzodiazepines, a method for reducing amounts and(or) side effects of benzodiazepines administered to a mammal which comprises administering to such mammal an effective amount of compound A in combination with benzodiazepines, a method for reducing amounts and(or) side effects of active component(s) (zolpidem, zopiclone, triazolam and/or brotizolam) administered to a mammal for treating or preventing sleep disorders which comprises administering to such mammal an effective amount of compound A in combination with at least one active component selected from zolpidem, zopiclone, triazolam and brotizolam, and a pharmaceutical composition for treating or preventing sleep disorders which comprises compound A in combination with at least one active component selected from non-benzodiazepines, etc.

Compound A used in the present invention can be produced by the methods disclosed in Example 11 of WO 97/32871 or analogous methods thereto.

Zolpidem is N,N, 6-trimethyl-2-(4-methylphenyl)-imidazo[1,2-a]pyridine-3-acetamide and can be produced by the methods disclosed in Japanese Patent Unexamined Publication No. 8384/1988 (S63) (U.S. Pat. No. 4,794,185) or analogous methods thereto.

Zopiclone is 4-methyl-1-piperazinecarboxylic acid 6-(5-chloro-2-pyridinyl)-6,7-dihydro-7-oxo-5H-pyrrolo[3,4-b]pyrazin-5-yl ester and can be produced by the methods disclosed in Japanese Patent Unexamined Publication No. 76892/1973(S48) (U.S. Pat. No. 3,862,149) or analogous methods thereto.

Triazolam (halcion) is 8-chloro-6-(2-chlorophenyl)-1-methyl-4H-[1,2,4]triazolo[4,3-a][1,4]benzodiazepine and can be produced by the methods disclosed in Japanese Patent Unexamined Publication No. 76892/1973(S48) (U.S. Pat. No. 3,987,052) or analogous methods thereto.

Brotizolam (lendormin) is 8-bromo-6-(o-chlorophenyl)-1-methyl-4H-s-triazolo[3,4c]thieno[2,3e]1,4-diazepine and can be produced by the methods disclosed in Japanese Patent Unexamined Publication No. 80899/1976(S51) (U.S. Pat. No. 4,094,984) or analogous methods thereto.

The pharmaceutical composition for treating or preventing sleep disorders in the present invention comprises compound A in combination with at least one active component selected from zolpidem, zopiclone, triazolam and brotizolam as active components. This composition can be used orally in the form of a dosage form available for each of the above components or by mixing each of the above components with a pharmacologically acceptable carrier or excipient and then combining them.

The pharmaceutical composition for treating or preventing sleep disorders in the present invention can be provided with compound A in combination with at least one active component selected from zolpidem, zopiclone, triazolam and brotizolam, for example, in the alternative forms prepared by the following procedures. (1) the above components are mixed optionally with a pharmaceutically acceptable excipient or the like by the known pharmaceutical technology to provide one dosage form, (2) the respective components are independently processed, optionally together with a pharmaceutically acceptable excipient or the like, to use in combination with independent dosage forms, at the same time or at staggered times, or (3) the respective components are independently processed, optionally together with a pharmaceutically acceptable excipient or the like, to provide independently prepared dosage forms as a set (kit). In the pharmaceutical composition of the present invention, in the case that the respective components are independently processed to provide independently prepared dosage forms, they can be administered to one patient at the same time or at staggered times, and the numbers of doses of the respective dosage forms may or may not be equal.

The pharmaceutical composition for treating or preventing sleep disorders in the present invention can be provided in one dosage form containing all of the active components or in dosage forms in which the respective active components or part of them are independently prepared. The amount of active components is from about 0.01 to about 100% by weight of the total weight of the composition. This composition can be administered to patients by the oral route, such as tablets, fine granules, capsules and granules, among others. Preferred are tablets, fine granules, and capsules.

The pharmaceutical compositions in the present invention can be formulated in any per se known manner or analogous methods thereof available with pharmaceutically acceptable carriers used in any per se known manner.

The said carriers include any ordinary organic and inorganic carrier substances that are usable in formulating medicines. For example, employable are excipients, lubricants, binders, disintegrators, etc. for formulating solid preparations; and solvents, solubilizers, suspending agents, isotonizing agents, buffers, soothing agents, etc. for formulating liquid preparations. If desired, further employable are other additives such as ordinary preservatives, antioxidants, colorants, sweeteners, adsorbents, wetting agents, etc.

The excipients include, for example, lactose, white sugar, D-mannitol, starch, corn starch, crystalline cellulose, light silicic anhydride, etc.

The lubricants include, for example, magnesium stearate, calcium stearate, talc, colloidal silica, etc.

The binders include, for example, crystalline cellulose, white sugar, D-mannitol, dextrin, hydroxypropyl cellulose, hydroxypropylmethyl cellulose, polyvinyl pyrrolidone, starch, sucrose, gelatin, methyl cellulose, carboxymethyl cellulose sodium, etc.

The disintegrators include, for example, starch, carboxymethyl cellulose, carboxymethyl cellulose calcium, croscarmellose sodium, carboxymethyl starch sodium, L-hydroxypropyl cellulose, etc.

The solvents include, for example, water for injections, alcohol, propylene glycol, macrogol, sesame oil, corn oil, olive oil, etc.

The solubilizers include, for example, polyethylene glycol, propylene glycol, D-mannitol, benzyl benzoate, ethanol, trisaminomethane, cholesterol, triethanolamine, sodium carbonate, sodium citrate, etc.

The suspending agents include, for example, surfactants such as stearyl triethanolamine, sodium lauryl sulfate, lauryl aminopropionic acid, lecithin, benzalkonium chloride, benzethonium chloride, glycerin monostearate, etc.; hydrophilic polymers such as polyvinyl alcohol, polyvinyl pyrrolidone, carboxymethyl cellulose sodium, methyl cellulose, hydroxymethyl cellulose, hydroxyethyl cellulose, hydroxypropyl cellulose, etc.

The isotonizing agents include, for example, glucose, D-sorbitol, sodium chloride, glycerin, D-mannitol, etc.

The buffers include, for example, liquid buffers of phosphates, acetates, carbonates, citrates, etc.

The soothing agents include, for example, benzyl alcohol, etc.

The preservatives include, for example, parahydroxybenzoates, chlorobutanol, benzyl alcohol, phenethyl alcohol, dehydroacetic acid, sorbic acid, etc.

The antioxidants include, for example, sulfites, ascorbic acid, etc.

The stabilizers for light include, for example, titanium oxide, etc.

The pharmaceutical composition containing compound A used in the present invention can be provided in various dosage forms, for example, as tablets (including sugar-coated tablets, film-coated tablets), powders, granules, capsules (including soft capsules), liquids, injections, suppositories, sustained release preparations, plasters and also as chewing gum, etc., in accordance with the per se known methods, for example, the methods disclosed in WO 97/32871 or analogous methods thereto.

The pharmaceutical composition which comprises at least one component selected from zolpidem, zopiclone, triazolam and brotizolam can be prepared in the same manner used in the above pharmaceutical composition containing compound A.

The pharmaceutical composition for treating or preventing sleep disorders which comprises compound A in combination with at least one active component selected from zolpidem, zopiclone, triazolam and brotizolam can reduce the amount (dose) of active component(s) required compared to the case with the monotherapy using any of the above-mentioned active components. Namely, in the present invention, it is preferred to use zolpidem, zopiclone, triazolam and brotizolam in a lower amount than the case with monotherapy using their active components for treating or preventing sleep disorders. In the present invention, for example, a combination of active component(s) in the respective amount of which separately cannot produce beneficial effects exhibits an action for sleep and reduces problematic side effects (e.g. rebound insomnia, dysmnesia, ataxia after awaking from sleep and somnolence). In other words, in the present invention, the amount of zolpidem, zopiclone, triazolam and/or brotizolam can be reduced to an amount which does not produce side effects and an effect for sleep can be produced with the lower amount.

Compound A does not produce side effects in a monotherapy dose.

The pharmaceutical composition for treating or preventing sleep disorders which comprises compound A in combination with at least one active component selected from zolpidem, zopiclone, triazolam and brotizolam is useful for treating and/or preventing, for example, sleep disorders [e.g., primary insomnia, sleep-awake rhythm disorders (e.g., work-shift syndrome, time-zone syndrome (jet-lag)), seasonal melancholia, genital disorder, neuroendocrine disorder, senile dementia, Alzheimer's disease, various disorders accompanied by aging, cerebrovascular disorders (e.g. cerebral hemorrhage, etc.), cranial injury, spinal injury, epilepsy, anxiety, depression, manic-depressive psychosis, schizophrenia, alcoholism, Parkinson's disease, hypertension, arteriosclerosis, arrhythmia, premenstrual tension syndrome, glaucoma, cancer, AIDS and diabetes in mammals (e.g. human, cat, dog, monkey, etc.). In addition, it is also effective for protection against aging, immunoregulation, and ovulatory regulation (e.g., contraception). Compound A is independently useful for treating and/or preventing, for example, sleep disorders (e.g., primary insomnia), sleep-awake rhythm disorders (e.g. work-shift syndrome, time-zone syndrome (jet-lag)), seasonal melancholia, genital disorder, neuroendocrine disorder, senile dementia, Alzheirner's disease, various disorders accompanied by aging, cerebrovascular disorders (e.g. cerebral hemorrhage, etc.), cranial injury, spinal injury, epilepsy, anxiety, depression, manic-depressive psychosis, schizophrenia, alcoholism, Parkinson's disease, hypertension, arteriosclerosis, arrhythmia, premenstrual tension syndrome, glaucoma, cancer, AIDS and diabetes in mammals (e.g. human, cat, dog, monkey, etc.). In addition, it is also effective for protection against aging, immunoregulation, and ovulatory regulation (e.g., contraception).

The pharmaceutical composition for treating or preventing sleep disorders in the present invention is of low toxicity and can be used safely for human with oral administration.

Though the dose of the pharmaceutical composition of the present invention varies, depending on the subject to which the composition is administered, the administration route employed, the disorder of the subject, the kinds of active components used, etc., for example, as the respective active components dose for adults (body weight about 60 kg) with sleep disorders, the following amount may be administered once or several times a day, at the same time or at an interval of 30 minutes or 3 hours.

The dose of compound A may be from about 0.05 to about 10 mg preferably from about 0.1 to about 3 mg for one administration.

The dose of zolpidem may be from about 0.2 to about 10 mg preferably from about 0.5 to about 5 mg for one administration.

The dose of zopiclone may be from about 0.2 to about 10 mg of, preferably from about 0.5 to about 5 mg of for one administration.

The dose of triazolam may be from about 0.01 to about 0.5 mg, preferably from about 0.02 to about 0.3 mg for one administration.

The dose of brotizolam may be from about 0.01 to about 1 mg preferably from about 0.05 to about 0.3 mg for one administration.

In the pharmaceutical composition for treating or preventing sleep disorders in the present invention, the ratio in combination of compound A with at least one selected from zolpidem, zopiclone, triazolam and brotizolam (relative dosage) is 0.1 to 30 part by weight per 1 part by weight of compound A.

The pharmaceutical composition for treating or preventing sleep disorders in the present invention may be used with other active components (e.g., benzodiazepine-type medicines comprising benzodiazepine compounds such as diazepam, alprazolam, estazolam, etc.; agents for regulating sleep rhythm comprising fatty acid derivatives such as butoctamide and its salt, etc.; sleep reducing substances comprising cis-9,10-octadecenamide, etc. Such other active components and the compound A and at least one active component selected from zolpidem, zopiclone, triazolam and brotizolam may be mixed by means of per se known methods to give pharmaceutical compositions (e.g., tablets, powders, granules, capsules including soft capsules, liquids, injections, suppositories, sustained release preparations, etc.); or they may be separately formulated into different preparations, which may be administered to one and the same subject either simultaneously or at different times.

BEST MODE FOR CARRYING OUT THE INVENTION

The invention will be described in more detail hereinafter, with reference to the following Reference Examples, Preparation Examples and Experimental Examples, which, however, are to concretely illustrate some embodiments of the invention and are not intended to restrict the scope of the invention. Various changes and modifications can be made within the range that does not deviate from the scope of the invention.

EXAMPLES

Reference Example 1

2,3-Dihydrobenzofuran-5-carbaldehyde

To a solution of 2,3-dihydrobenzofuran (100.0 g, 832 mmols) in N,N-dimethylformamide (134.0 g, 1.83 mols) was added dropwise phosphorus oxychloride (255.1 g, 1.66 mols), then the mixture was stirred at 80–90° C. for 7.5 hours. The mixture was cooled to room temperature, poured into water (1 L) and stirred for 15 hours. The product was extracted with toluene (1.5 L). The extract was washed with water (500 mL) followed by a saturated aqueous solution of sodium bicarbonate (500 mL) and concentrated under reduced pressure to obtain 115.9 g (yield: 94%) of the title compound.

Reference Example 2

Ethyl (E)-3-(2,3-Dihydrobenzofuran-5-yl)-2-propenoate

To an ice-cooled suspension of sodium t-butoxide (90.4 g, 941 mmols) in toluene (1 L) was added dropwise triethyl phosphonoacetate (211.0 g, 941 mmols) followed by 2,3-dihydrobenzofuran-5-carbaldehyde (115.9 g 782 mmols). The mixture was stirred for 1 hour and then acetic acid (12 g, 200 mmols) and water (604 mL) was added. The separated organic layer was washed with water (525 mL) followed by a saturated aqueous solution of sodium bicarbonate (263 mL) and concentrated under reduced pressure. Methanol (525 mL) and water (525 mL) were added to the residue and the mixture was stirred for 30 minutes. Crystals precipitated were collected by filtration to obtain 161.2 g (yield: 94%) of the title compound.

Reference Example 3

Ethyl 3-(2,3-Dihydrobenzofuran-5-yl)propionate

To a solution of ethyl (E)-3-(2,3-dihydrobenzofuran-5-yl)-2-propenoate (160.0 g, 733 mmols) in acetic acid (960 mL) was added 5% palladium on activated carbon (32.0 g, 50% hydrous). The mixture was stirred at 50° C. for 3.5 hours under hydrogen atmosphere (ambient pressure). The catalyst was filtered off and the filtrate containing 156.7 g (yield: 97%) of the title compound was obtained which was provided to the next step.

Reference Example 4

3-(6,7-Dibromo-2,3-dihydrobenzofuran-5-yl) propionic Acid

Sodium acetate (59.2 g, 722 mmols) was dissolved in a solution of ethyl 3-(2,3-dihydrobenzofuran-5-yl)propionate (156.7 g, 711 mmols) in acetic acid, which was obtained in Reference Example 3. To the solution was added dropwise bromine (708 g, 4.43 mols). The reaction mixture was stirred at room temperature for 4 hours and then added to a precooled 15% aqueous solution of sodium sulfite (2527 g) followed by refluxing with acetonitrile (480 mL) for 2 hours. After cooling, crystals were collected by filtration and washed with water to obtain 179.3 g (yield: 72%) of the title compound.

Reference Example 5

4,5-Dibromo-1,2,6,7-tetrahydro-8H-indeno[5,4-b]furan-8-one

A mixture of 3-(6,7-dibromo-2,3-dihydrobenzofuran-5-yl)propionic acid (10.0 g, 28.6 mmols), dichloromethane (35 mL), thionyl chloride (5.11 g, 40.8 mmols) and N,N-dimethylformamide (30 mg) was heated to reflux for 1 hour. After cooling, aluminum chloride (4.66 g, 43.3 mmols) was added to the reaction mixture a trot more than 0° C. and then the mixture was stirred for 30 min. The reaction mixture was poured into precooled methanol (200 mL), then stirred for 30 min. Crystals precipitated were collected by filtration, washed with water (500 mL) followed by methanol (500 mL) to obtain 7.9 g (yield: 89%) of the title compound.

Reference Example 6

1,2,6,7-Tetrahydro-8H-indeno[5,4-b]furan-8-one

To a suspension of 4,5-dibromo-1,2,6,7-tetrahydro-8H-indeno[5,4-b]furan-8-one (18.4 g, 55.4 mmols) in methanol (400 mL) was added 10% Palladium on activated carbon (2.0 g, 50% hydrous) followed by sodium acetate (12.6 g, 154 mmols). The mixture was stirred at 40° C. for 1.5 hours under hydrogen atmosphere (4 kgf/cm$^2$). The catalyst was filtered off and the filtrate was concentrated under reduced pressure. Crystals were collected by filtration, washed with water and recrystallized successively with methanol:water= 5:1 to obtain 8.0 g (yield: 83%) of the title compound.

Reference Example 7

(E)-(1,6,7,8-Tetrahydro-2H-indeno[5,4-b]furan-8-ylidene)acetonitrile

To a solution of 1,2,6,7-tetrahydro-8H-indeno[5,4-b]furan-8-one (250.0 g, 1.44 mols) and diethyl (cyanomethyl)phosphonate (304.8 g, 1.72 mols) in toluene (6.25 L) was added dropwise 28% sodium methoxide in methanol (332.8 g, 1.72 mols). After stirring for 2 hours under the same temperature, water (2.5 L) was added to the reaction mixture to separate the organic layer which was washed with water (1 L) and concentrated under reduced pressure. Crystals were collected by filtration to obtain 250.4 g (yield: 88%) of the title compound.

Reference Example 8

(E)-2-(1,6,7,8-Tetrahydro-2H-indeno[5,4-b]furan-8-indene)ethylamine Hydrochloride To a solution of (E)-(1,6,7,8-tetrahydro-2H-indeno[5,4-b]furan-8-ylidene)acetonitrile (30.0 g, 152 mmols) in toluene (500 mL) were added methanol (100 mL), 14.4% aqueous solution of sodium hydroxide (10.5 g) and Raney cobalt (44 g). The mixture was stirred at 35° C. for 5.5 hours under hydrogen atmosphere (2 kgf/cm$^2$). After the catalyst was filtered off, water (160 mL) and 1N-HCl (150 mL) were added to the filtrate, then the mixture was stirred at 40° C. for 30 min. The aqueous layer was separated and a saturated aqueous solution of sodium chloride (320 mL) was added. The precipitated crystals were collected by filtration to obtain 30.0 g (yield: 83%) of the title compound.

Reference Example 9

(S)-2-(1,6,7,8-Tetrahydro-2H-indeno[5,4-b]furan-8-yl] ethylamine Hydrochloride

A Hastelloy autoclave (200 mL) was charged with (E)-2-(1,6,7,8-tetrahydro-2H-indeno[5,4-b]furan-8-ylidene)ethylamine (1.00 g, 5.00 mmol.), Ru$_2$Cl$_4$[(R)-BINAP]$_2$NEt$_3$ (21.0 mg) and methanol (10 mL) under nitrogen atmosphere. Into the vessel, hydrogen gas was introduced up to 100 atmospheric pressure. The mixture was stirred for 20 hours at 50° C. The reaction system was depressurized to normal, followed by determination of the conversion and the optical purity of the product, (S)-2-(1,6,7,8-tetrahydro-2H-indeno[5,4-b]furan-8-yl) ethylamine), by means of high performance liquid chromatography. The conversion was 100% and the optical purity was 88.8% e.e.

Toluene (10 mL) was added to the residue (1.02 g) obtained by concentration under reduced pressure. The mixture was cooled on an ice-bath, to which was added, while stirring, 2% hydrochloric acid (10 mL). The reaction mixture was stirred for 30 minutes, which was concentrated under reduced pressure to leave the residue (1.21 g). The concentrate was dissolved in methanol (5 mL), to which was added acetone (10 mL). The mixture was cooled to 0° C., which was then subjected to filtration to collect the title compound (0.64 g). Further, the filtrate was concentrated under reduced pressure. The concentrate (0.34 g) was recrystallized from a mixture of methanol (1.5 mL) and acetone (3.0 mL) to give the title compound (0.17 g, total yield 0.81 g, yield 68%). This hydrochloride was processed with a 5% aqueous solution of sodium hydroxide to give (S)-2-(1,6,7,8-tetrahydro-2H-indeno[5,4-b]furan-8-yl) ethylamine. The optical purity of the product was determined by means of high performance liquid chromatography, which was 100% e.e.

Reference Example 10

(S)-N-[2-(1,6,7,8-Tetrahydro-2H-indeno[5,4-b]furan-8-yl)ethyl]propionamide (compound A)

To a suspension of (S)-2-(1,6,7,8-tetrahydro-2H-indeno[5,4-b]furan-8-yl)ethylamine hydrochloride (100.0 g, 417 mmol) in tetrahydrofuran (250 mL) at 15° C. was added dropwise a 7.1% aqueous solution of sodium hydroxide (538 mL). Propionyl chloride (44.4 g, 480 mmol) was added dropwise to the reaction mixture. Stirring was continued at room temperature for 30 min. Water (800 mL) was added and crystals precipitated were collected by filtration followed by recrystallization from ethanol:water=1:2 to obtain 99.5 g (yield: 92%) of the title compound.

Preparation Example 1

| | |
|---|---|
| (1) compound A | 10.0 g |
| (2) lactose | 60.0 g |
| (3) corn starch | 35.0 g |

-continued

|  |  |  |
|---|---|---|
| (4) | gelatin | 3.0 g |
| (5) | magnesium stearate | 2.0 g |

Compound A (10.0 g), lactose (60.0 g) and corn starch (35.0 g) were mixed and the mixture was granulated with 10% (w/v) aqueous solution dissolving gelatin (gelatin 3.0 g) by using a screen with 1 mm mesh, and was dried at 40° C. and screened. Thus-obtained granules were mixed with magnesium stearate (2.0 g) and compressed to give uncoated-tablets. The uncoated-tablets were sugar-coated with a fluid containing cane sugar, titanium dioxide, talc and arabic gum and polished with beeswax to give 1000 coated tablets.

Preparation Example 2

|  |  |  |
|---|---|---|
| (1) | compound A | 10.0 g |
| (2) | lactose | 70.0 g |
| (3) | corn starch | 50.0 g |
| (4) | soluble starch | 7.0 g |
| (5) | magnesium stearate | 3.0 g |

Compound A (10.0 g) and magnesium stearate (3.0 g) were granulated with 70 mL of aqueous solution dissolving soluble starch (7.0 g of soluble starch). The granules were dried and mixed with lactose (70.0 g) and corn starch (50.0 g). The mixtures were compressed to give 1000 tablets.

Preparation Example 3

|  |  |  |
|---|---|---|
| (1) | compound A | 1.0 g |
| (2) | lactose | 60.0 g |
| (3) | corn starch | 35.0 g |
| (4) | soluble starch | 3.0 g |
| (5) | magnesium stearate | 2.0 g |

Compound A (1.0 g), lactose (60.0 g) and corn starch (35.0 g) were mixed and the mixture was granulated with 30 mL of 10% (w/v) aqueous solution dissolving gelatin (gelatin 3.0 g) by using a screen with 1 mm mesh, and was dried at 40° C. and screened. The thus-obtained granules were mixed with magnesium stearate (2.0 g) and compressed to give uncoated-tablets. The uncoated-tablets were sugar-coated with a fluid containing cane sugar, titanium dioxide, talc and arabic gum and polished with beeswax to give 1000 coated tablets.

Experimental Example

Methods

Six female crab-eating macaques (*Macaca fascicularis*), weighing 2.8–4.2 kg, were housed individually in a room maintained at 24±1° C. with a 12-h light/dark cycle (light on 6:00). Under sodium pentobarbital anesthesia, stainless steel screw and bipolar electrodes for electroencephalogram (EEG), electromyogram (EMG) and electro-oculogram (EOG) were implanted. After recovery from surgery, the monkeys were well habituated to the recording chamber (60×60×80 cm) located in a sound-proof and electrically shielded room. Compound A (0.003 mg/kg) and/or triazolam (0.03 mg/kg) were given orally 17:50–17:55. Compound A and triazolam were suspended in 0.5% methylcellulose solution. The control monkey was given 0.5% MC. The behaviors of subjects were observed using a video camera with infrared light sensitivity. EEG, EMG and EOG were recorded on a MO disk with an electroencephalograph (EE5518, NEC Medical Systems, Tokyo, Japan). All recordings were carried out from 18:00 until 6:00. The EEG power spectral analysis was also performed continuously by means of a fast Fourier transform (FFT) system equipped with a personal computer. Based on these EEG, EMG and EOG data and on behavior, visually judged in each 20-sec epoch, we classified the sleep-wake stages according to Rechtshaffen and Kales (1968) essentially (i.e. stage W, stage 1+2, stage 3, stage 4 and stage rapid eye movement (REM)). Latencies of each sleep stage (the time until the first appearance of each sleep stage) were determined from 18:00. The occurrence of each sleep stage at nighttime and other sleep parameters were also determined.

Results

Treatment with compound A (0.003 mg/kg, p.o.) had no significant effects on the latency of any sleep stages. Triazolam (0.03 mg/kg, p.o.) alone also produced no significant effects on the sleep latencies. Treatment with triazolam (0.03 mg/kg) did not affect general behavior and it did not cause ataxia and sedation as such were seen when high doses of triazolam are given. The effects of co-administration of compound A and triazolam on the sleep latency are shown in FIG. 1. Co-administration of Compound A and triazolam shortened the latencies of deep slow wave sleep, stage 3 and stage 4, and it significantly shortend the latency of the stage 4 sleep. The co-administration also had no significant effects on general behavior of monkeys.

It is clear that compound A in combination with triazolam has an excellent effect on sleep disorders without side effects. (Rechtschaffen, A. and Kales, A. A.: A Manual of Standardized Terminology, Techniques and Scoring System for Sleep Stages of Human Subjects. Bethersda, M. D., US Department of Health, Education and Welfare, 1968.)

Industrial Applicability

The pharmaceutical composition for treating or preventing sleep disorders which comprises (S)-N-[2-(1,6,7,8-tetrahydro-2H-indeno[5,4-b]furan-8-yl)ethyl]propionamide (compound A) in combination with at least one active component selected from zolpidem, zopiclone, triazolam and brotizolam in one dosage form or independent dosage forms and the method for treating or preventing which comprises administering the composition to a mammal is useful for treating and/or preventing, for example, sleep disorders (e.g., primary insomnia), sleep-awake rhythm disorders (e.g. work-shift syndrome, time-zone syndrome (jet-lag)), seasonal melancholia, genital disorder, neuroendocrine disorder, senile dementia, Alzheimer's disease, various disorders accompanied by aging, cerebrovascular disorders (e.g. cerebral hemorrhage, etc.), cranial injury, spinal injury, epilepsy, anxiety, depression, manic-depressive psychosis, schizophrenia, alcoholism, Parkinson's disease, hypertension, arteriosclerosis, arrhythymia, premenstrual tension syndrome, glaucoma, cancer, AIDS and diabetes in mammals (e.g. human, cat, dog, monkey, etc.). In addition, it is also effective for protection against aging, immunoregulation, and ovulatory regulation (e.g., contraception). Compound A is independently useful for treating and/or preventing, for example, sleep disorders (e.g., primary insomnia), sleep-awake rhythm disorders (e.g. work-shift syndrome, time-zone syndrome (jet-lag)), seasonal melancholia, genital disorder, neuroendocrine disorder, senile dementia, Alzheimer's disease, various disorders accompanied by aging, cerebrovascular disorders (e.g. cerebral hemorrhage, etc.), cranial injury, spinal injury, epilepsy, anxiety, depression, manic-depressive psychosis, schizophrenia, alcoholism, Parkinson's disease, hypertension, arteriosclerosis, arrhythmia, premenstrual tension syndrome, glaucoma, cancer, AIDS and diabetes in mammals (e.g. human, cat, dog, monkey, etc.). In addition, it is also effective for protection against aging,

What is claimed is:

1. A method for treating sleep disorders in a mammal comprising administering to a mammal in need thereof a combination of
   a first component, (S)-N-[2-(1,6,7,8-tetrahydro-2H-indeno[5,4-b]furan-8-yl)ethyl]propionamde,
      wherein the amount of said first component is an amount ineffective for inducing sleep when administered alone; and
   a second component, at least one active component selected from the group consisting of zolpidem, zopiclone, brotizolam and triazolam,
      wherein the amount of said second component is an amount ineffective for inducing sleep when administered alone; such that said combination induces sleep.

2. A method for treating sleep disorders in a mammal comprising administering to a mammal in need thereof a combination of
   a first component, (S)-N-[2-(1,6,7,8-tetrahydro-2H-indeno[5,4-b]furan-8-yl)ethyl]propionamde,
      wherein the amount of said first component is an amount ineffective for inducing sleep when administered alone; and
   a second component, triazolam,
      wherein the amount of said second component is an amount ineffective for inducing sleep when administered alone; such that said combination induces sleep.

* * * * *